(12) United States Patent
Weekamp et al.

(10) Patent No.: US 7,955,558 B2
(45) Date of Patent: Jun. 7, 2011

(54) DEVICE FOR TESTING A FLUID

(75) Inventors: Johannes Wilhelmus Weekamp, Eindhoven (NL); Menno Willem Jose Prins, Eindhoven (NL); Albert Hendrik Jan Immink, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 376 days.

(21) Appl. No.: 12/092,840

(22) PCT Filed: Oct. 30, 2006

(86) PCT No.: PCT/IB2006/054001
§ 371 (c)(1),
(2), (4) Date: May 7, 2008

(87) PCT Pub. No.: WO2007/054850
PCT Pub. Date: May 18, 2007

(65) Prior Publication Data
US 2008/0247910 A1 Oct. 9, 2008

(30) Foreign Application Priority Data
Nov. 9, 2005 (EP) ..................... 05110523

(51) Int. Cl.
*G01N 15/06* (2006.01)
*G01N 33/00* (2006.01)
*G01N 33/48* (2006.01)
*G01N 27/00* (2006.01)
*G01N 31/22* (2006.01)
*G01N 33/52* (2006.01)
*B01L 3/00* (2006.01)

(52) U.S. Cl. ................. 422/68.1; 422/82.01; 422/430; 422/501

(58) Field of Classification Search .................. None
See application file for complete search history.

(56) References Cited

U.S. PATENT DOCUMENTS

| 4,618,476 | A | 10/1986 | Columbus |
| 6,019,944 | A | 2/2000 | Buechler |
| 6,150,178 | A * | 11/2000 | Cesarczyk et al. ............ 436/165 |
| 6,292,126 | B1 | 9/2001 | Chelehmal et al. |
| 6,911,183 | B1 | 6/2005 | Handique et al. |
| 7,303,923 | B2 * | 12/2007 | Hardman et al. .............. 436/518 |
| 2002/0019062 | A1 * | 2/2002 | Lea et al. ....................... 436/518 |

(Continued)

FOREIGN PATENT DOCUMENTS

| EP | 0320240 A1 | 6/1989 |
| WO | WO9011519 A1 | 10/1990 |
| WO | WO9217778 A1 | 10/1992 |
| WO | WO0057179 A1 | 9/2000 |

(Continued)

*Primary Examiner* — Jill Warden
*Assistant Examiner* — Charles Hammond

(57) ABSTRACT

A device for testing a fluid including an elongated carrier; two foam members for absorbing the fluid, which are arranged at an end of the carrier; a positioning member having a sleeve which is slidably arranged on the carrier; and a diagnostic device, which is arranged in the positioning member having a sensor die adapted to detecting at least one property of the fluid and means for supplying the fluid to a sensor surface of the sensor die. After the fluid has been supplied to the foam members, the positioning member is moved towards the end of the carrier where the foam members are located. When the diagnostic device comes into contact with one of the foam members, the fluid is squeezed from the foam member and supplied to the sensor surface of the sensor die through the fluid supplying means of the diagnostic device.

13 Claims, 10 Drawing Sheets

U.S. PATENT DOCUMENTS

| | | | |
|---|---|---|---|
| 2002/0106809 A1* | 8/2002 | Cesarczyk | 436/165 |
| 2004/0072357 A1 | 4/2004 | Stiene et al. | |
| 2004/0182703 A1* | 9/2004 | Bell et al. | 204/403.11 |
| 2005/0106756 A1 | 5/2005 | Blankenstein et al. | |
| 2005/0136551 A1 | 6/2005 | Mpock | |

FOREIGN PATENT DOCUMENTS

| | | |
|---|---|---|
| WO | WO0204942 A1 | 1/2002 |
| WO | WO2004065010 A2 | 8/2004 |
| WO | WO2005003723 A2 | 1/2005 |
| WO | WO2005088300 A1 | 9/2005 |

* cited by examiner

DEVICE FOR TESTING A FLUID

The present invention relates to a device for testing a fluid.

In various fields, including the fields of point-of care diagnostics and roadside drug abuse testing, there is a great need for a compact testing device, which is easy to use, and which is capable of yielding fast results.

US 2005/0136551 discloses a system which includes a disposable plastic strip that can be inserted into a portable handheld analyzer. The disposable strip has a plurality of defined wells on a solid support, which are linked by capillary channels. To test a sample, the disposable strip is inserted into the analyzer, and a sample drop is placed in one of the wells of the strip. The sample fluid moves into the other wells via the capillary channels. One of these other wells serves as a reaction well, where individual components of the sample are identified by the analyzer. The analyzer includes a display system for displaying the results of the analysis.

It is an important objective of the present invention to provide a testing device which is easier to use than the system known from US 2005/0136551, so that the testing device is suitable to be used for the purpose of performing quick diagnostics tests at the local doctor or quick tests during surveillances of road users, for example. The objective is achieved by means of a testing device, comprising: a carrier; a member for receiving the fluid, which is arranged on the carrier; a positioning member which is slidably arranged on the carrier; and a diagnostic device, which is arranged in the positioning member, and which comprises sensitive means adapted to detecting at least one property of the fluid.

In the testing device according to the present invention, by means of the positioning member, it is possible to put the diagnostic device in various positions on the carrier. During a first step of a practical application of the testing device, the positioning member is held in an initial position on the carrier, in which the positioning member is located at a distance from the fluid receiving member, so that the fluid receiving member is free to receive the fluid. Subsequently, when the fluid needs to be tested, the positioning member is moved towards the fluid receiving member. When the positioning member has reached the fluid receiving member, the diagnostic device comes into contact with the fluid, and the test may be performed.

The fluid receiving member may comprise a member which is adapted to absorbing fluid, for example a foam member. In such a case, the testing device is suitable to be used for collecting fluid to be tested. Consequently, when the testing device is applied, there is no need for applying separate means for collecting the fluid, and there is no need for conveying the fluid from such means to the testing device. In view of the desire to have a testing device which is suitable to be applied for the purpose of performing point-of-care diagnostics tests or roadside tests, this is a very advantageous aspect of the present invention.

In a practical embodiment of the testing device according to the present invention, the diagnostic device further comprises means for supplying the fluid from the fluid receiving member to a sensitive surface of the sensitive means. Preferably, these fluid supplying means are adapted to taking in the fluid from the fluid receiving member when an inlet side of the fluid supplying means contacts the fluid receiving member and the fluid supplying means and the fluid receiving member are moved with respect to each other. In this way, it is achieved that all that is needed for conveying the fluid from the fluid receiving member to the sensitive surface of the sensitive means of the diagnostic device is that the positioning member is moved over the portion of the carrier where the fluid receiving member is located. For example, the fluid receiving member comprises foam, and the fluid is squeezed from the foam when the foam is impressed by a member which is located at the inlet side of the fluid supplying means of the diagnostic device.

According to a preferred option, the fluid supplying means of the diagnostic device are adapted to conveying the fluid on the basis of capillary forces, so that there is no need for additional means like a pump for the purpose of forcing the fluid to flow towards the sensitive surface of the sensitive means. In an advantageous embodiment, the fluid supplying means of the diagnostic device comprise a plate having a pattern of channels for conducting the fluid, which is present at one side of the plate. The plate may be manufactured in a relative simple way, for example by applying injection molding techniques. Furthermore, the plate does not require much space.

In many cases, it is required to put the fluid that needs to be examined into contact with at least one reagent first, before putting the fluid into contact with the sensitive surface of the sensitive means, so that the fluid is put in a state which is needed in view of examination by the sensitive means. For example, certain molecules which are present in the fluid are labeled in a manner known per se, so that the sensitive means are capable of detecting the molecules. Therefore, in a practical embodiment, the diagnostic device of the testing device comprises at least one reagent, wherein the fluid supplying means are adapted to putting the fluid into contact with the at least one reagent.

The carrier may be shaped like an elongated piece of strip, for example like a ruler. In such a case, the testing device is easy to handle by a user, namely by holding one end of the carrier. Furthermore, the positioning means may comprise a sleeve which is slidably arranged around the carrier.

In an advantageous embodiment, the testing device according to the present invention comprises two members for receiving the fluid, wherein each fluid receiving member is arranged at another side of the carrier. When this embodiment of the testing device is applied, the fluid may be collected at two places on the carrier, wherein the fluid which is present at one place may be tested by means of the diagnostic device, while the fluid which is present at another place may be stored and used for a countercheck at a later stage. Preferably, the positioning member is adapted to enclosing both fluid receiving members, so that it is not necessary to have additional means for the purpose of storing the fluid.

According to a practical possibility, the diagnostic device of the testing device comprises at least one electrically conductive connection pad for connection of the diagnostic device to another electric device, wherein the positioning means comprise at least one hole for providing access to the at least one connection pad. In such configuration, it is easy to connect a read-out unit or the like to the diagnostic device for retrieving information from the sensitive means. Within the scope of the present invention, it is also possible that the testing device itself comprises displaying means for generating a visual representation of output provided by the sensitive means during operation of the testing device. Furthermore, the diagnostic device of the testing device may comprise at least one processor die for processing output provided by the sensitive means during operation of the testing device.

In principle, the diagnostic device of the testing device may be any suitable diagnostic device comprising sensitive means. For example, the sensitive means may comprise a sensor die of a semiconductor material. In particular, the sensitive means may be adapted to determining a presence and/or a quantity of a compound of a fluid.

In a preferred embodiment, the diagnostic device comprises a body member having a recess in which the sensitive means are arranged, wherein a pattern of electrically conductive connection pads and electrically conductive tracks is arranged on the body member, at the side where the recess is present, wherein the sensitive means are connected to at least one of the connection pads, and wherein the body member has at least one hole providing access to the sensitive means from another side than the side where the recess and the electrically conductive pattern are present. Advantageously, the body member of the diagnostic device comprises at least one other recess, which is arranged at another side of the body member than the recess in which the sensitive means are present, and wherein at least one hole providing access to the sensitive means is present at a bottom of the at least one other recess. Such a diagnostic device is very well adapted to performing its functions. Furthermore, such a diagnostic device may be compact, with dimensions in the millimeter range.

It is noted that the testing device according to the present invention is particularly suitable for performing a test for the purpose of providing a first indication of one or more properties of a fluid, rather than performing a very accurate test. Therefore, the diagnostic device may be relatively simple, which is an advantage in case the testing device is a disposable. For sake of completeness, it is noted that in such a case, it is preferred if the testing device is used in combination with a read-out unit which is connectable to the testing device, so that only a limited number of components is thrown away when the testing device is thrown away.

The testing device according to the present invention may be adapted to indicating whether an individual has used drugs, or not. In such a case, the test may be performed on an amount of saliva of the individual in question. In a first step of the test, an end of the carrier of the testing device, in particular a saliva collecting end where the fluid receiving member is located, is inserted in the mouth of the individual, while the positioning member is kept in an initial position near another end of the carrier. In the process, saliva is collected in the fluid receiving member. After a short period of time, the saliva collecting end of the carrier is removed from the mouth of the individual, and the positioning member is slid across the carrier, in a direction towards the saliva collecting end. As soon as an inlet side of the fluid supplying means of the diagnostic device has reached the position of the fluid receiving member, and is moved further, saliva is taken in by the fluid supplying means and supplied to the sensitive surface of the sensitive means of the diagnostic device. The sensitive means of the diagnostic device detect one or more properties of the saliva, and a user of the testing device is informed about these properties, through a read-out unit which is connected to the diagnostic device of the testing device. In case the information points out that it is likely to assume that the tested individual has been using drugs, indeed, more accurate tests may be performed. In this case, it is advantageous if the testing device comprises an extra fluid receiving member at the saliva collecting end of the carrier, which is kept safely within the positioning member, as the saliva that has been collected by this fluid receiving member may very well be used for the purpose of performing an additional test.

The present invention will now be explained in greater detail with reference to the Figures, in which similar parts are indicated by the same reference signs, and in which.

Figure 11:
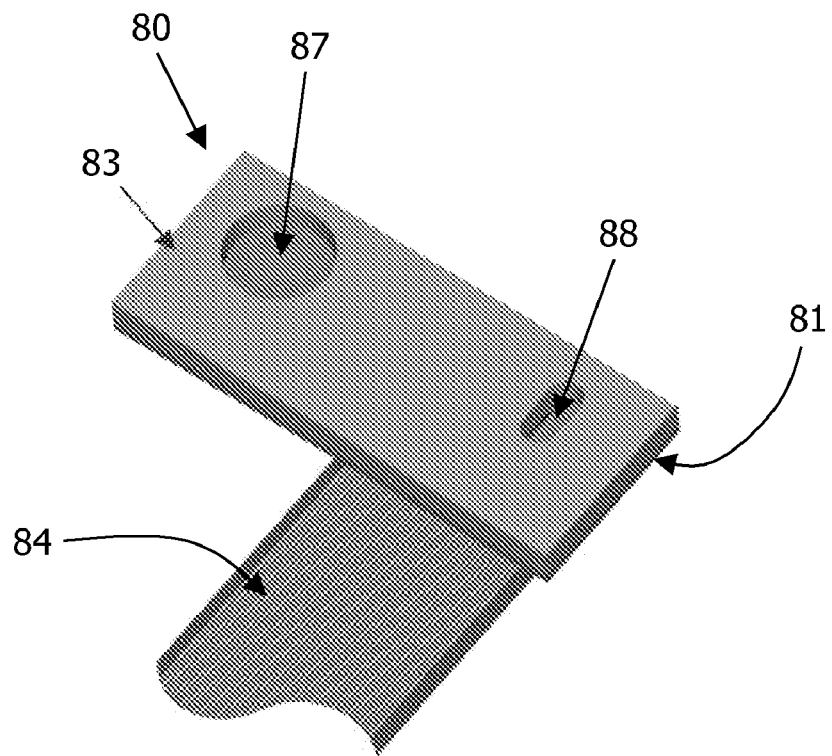
FIG. 11 shows an upper side of an assembly of the substrate, the sensor die and the microfluidic plate of the alternative testing device, wherein also a portion of an electric connection cable is shown.
Figure 12:
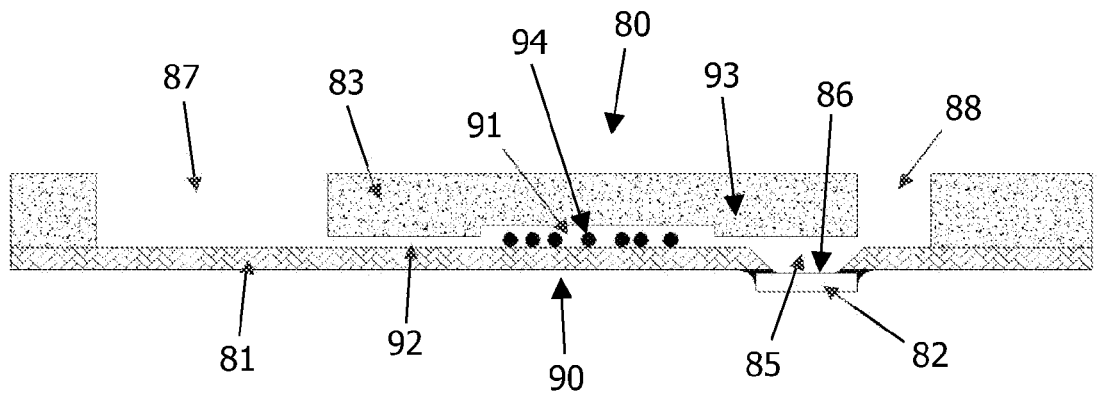
Figure 13A:
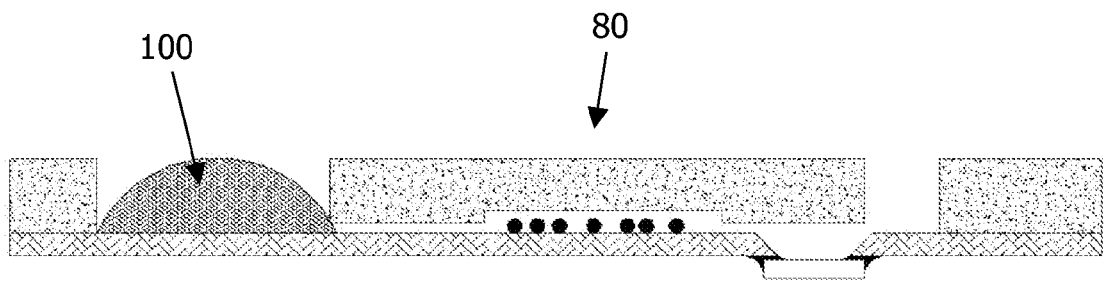
Figure 13B:
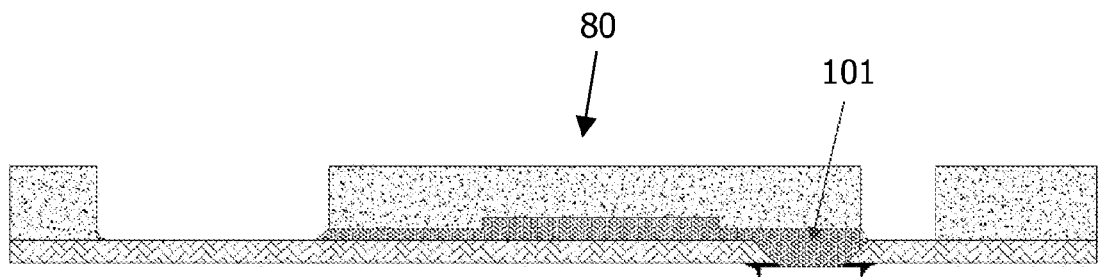

FIG. 12 diagrammatically shows a side view of a longitudinal section of the assembly shown in FIG. 11; and FIGS. 13a and 13b illustrate subsequent steps of a process of testing a droplet of saliva by means of the alternative testing device.

FIGS. 1a to 1h illustrate subsequent steps of a process of manufacturing a diagnostic device 2 of a testing device 1 according to a preferred embodiment of the present invention, which is particularly suitable for testing saliva. In the following, the manufacturing process will be described for one diagnostic device 2. Nevertheless, the diagnostic device 2 may be manufactured as part of an array of devices, wherein individual devices are eventually obtained by dicing the array.

In each of FIGS. 1c to 1h, both a perspective view of an under side of the diagnostic device 2 in the process of formation and a perspective view of an upper side of the diagnostic device 2 in the process of formation are shown. Furthermore, in FIG. 2, both a perspective view of an under side of a microfluidic plate 60 of the diagnostic device 2 and a perspective view of an upper side of this microfluidic plate 60 are shown.

Figure 1A:
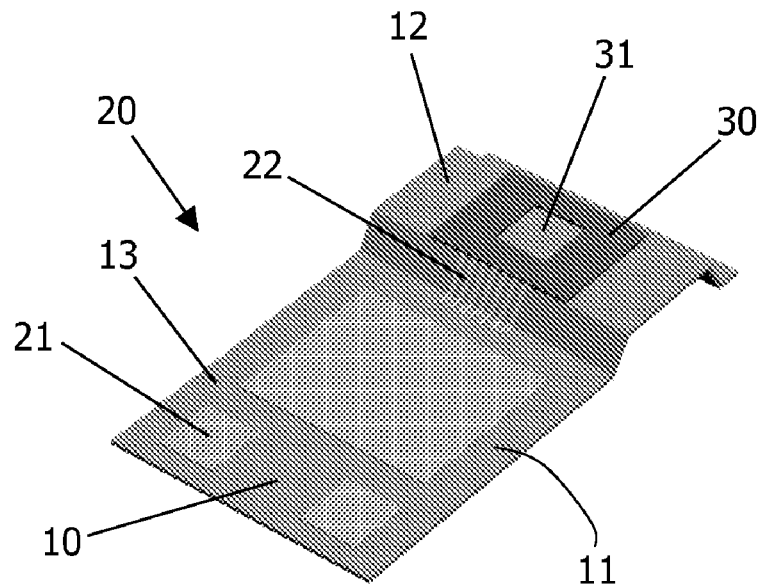
FIGS. 1a to 1h illustrate subsequent steps of a process of manufacturing a diagnostic device of a testing device according to a preferred embodiment of the present invention.

In a first step of the process of manufacturing the diagnostic device 2, which is illustrated by FIG. 1a, a sacrificial carrier 10 is provided. The carrier 10 comprises a sheet of material, for example copper. At a carrying surface 11, the carrier 10 is provided with a pattern 20 of electrically conductive connection pads 21 and electrically conductive tracks 22.

The carrier 10 is bent in such a way that two portions 12, 13 which are located at a different level are obtained. In particular, after bending of the carrier 10 has taken place, an elevated portion 12 and a recessed portion 13 of the carrying surface 11 are discernible. At the elevated portion 12 of the carrying surface 11 of the carrier 10, a thin layer 30 is applied. The layer 30 comprises electrically insulating material, for example a material known as solder resist, which is an organic material. At a central position, the layer 30 is interrupted, such that a central hole 31 is obtained in the layer 30. In the following, for sake of clarity, the layer 30 of electrically insulating material will be referred to as covering member 30.

Figure 1B:
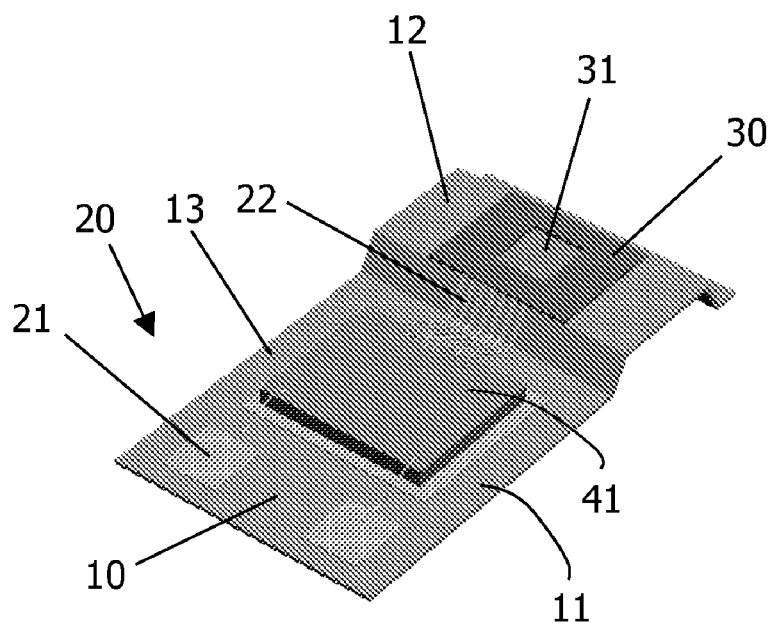

In a second step of the process of manufacturing the diagnostic device 2, which is illustrated by FIG. 1b, a processor die 41 or another suitable microelectronic element is positioned on the recessed portion 13 of the carrying surface 11 of the carrier 10, wherein electric connections between the processor die 41 and both the electrically conductive connection pads 21 and the electrically conductive tracks 22 of the pattern 20 are realized. In the process, any suitable technique for connecting a die to electrically conductive elements may be applied.

Figure 1C:
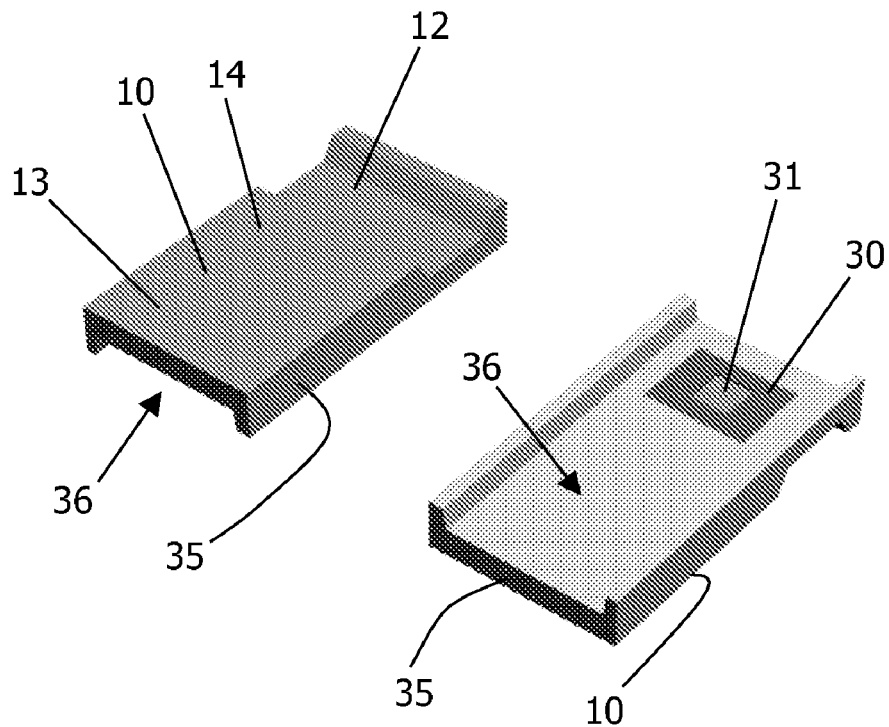

In a third step of the process of manufacturing the diagnostic device 2, which is illustrated by FIG. 1c, the carrier 10 and the components 20, 30, 41 arranged on its carrying surface 11 are overmolded with a suitable material, on the basis of which a body member 35 is formed on the carrier 10, at the side of the carrying surface 11. In the process, the processor die 41 gets encapsulated in the body member 35. Furthermore, in the process, a trough-like recess 36 is formed in the body member 35, wherein a top side of the covering member 30 is located at a bottom of the recess 36.

The body member 35 may be created and shaped by positioning the carrier 10 and the components 20, 30, 41 arranged on its carrying surface 11 in a mould (not shown) and introducing material for forming the body member 35 in this mould. Such a mould may for example comprise a bottom part and a top part, wherein a surface of the bottom part is complementary with an under surface 14 of the carrier 10, so that there is practically no space present between these surfaces when the carrier 10 is placed on the bottom part of the mould. The top part of the mould may comprise a corrugation for forming the recess 36 in the body member 35, wherein measures are taken to ensure that the corrugation contacts the covering member 30 when the material for forming the body member 35 is introduced in the mould, so that at least a portion of the covering member 30 comprising the hole 31 is left uncovered.

Figure 1D:
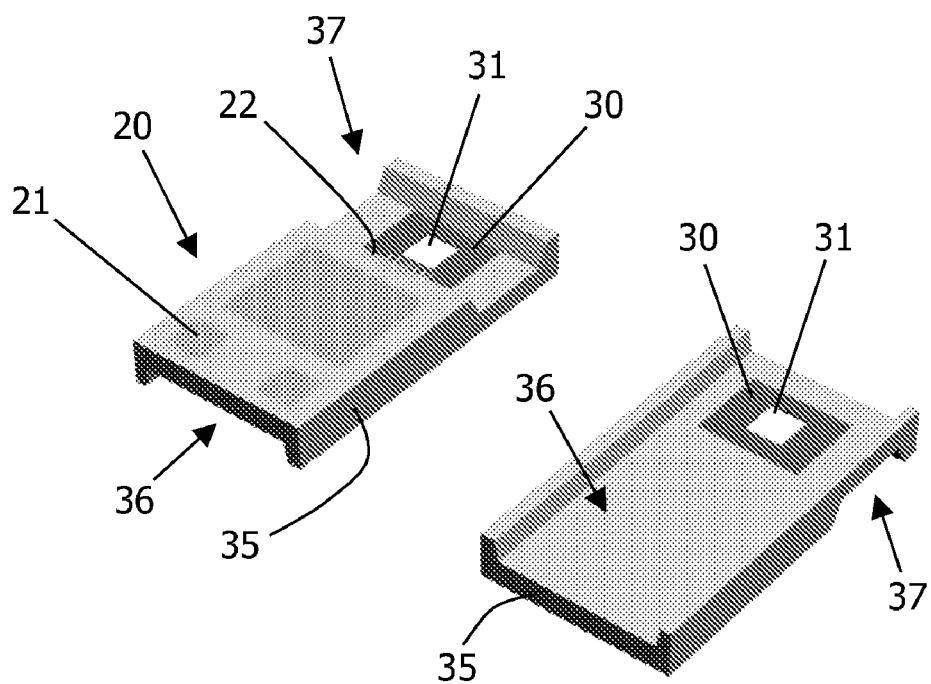

In a fourth step of the process of manufacturing the diagnostic device 2, which is illustrated by FIG. 1d, the carrier 10 is removed by chemical etching, peeling, or another suitable technique. At the under side of the body member 35, at the position where the elevated portion 12 of the carrier 10 has been, a through-like recess 37 has been formed, wherein the covering member 30 is present at a bottom of the recess 37. Furthermore, as a result of the removal of the carrier 10, the hole 31 of the covering member 30 is open.

Figure 1E:
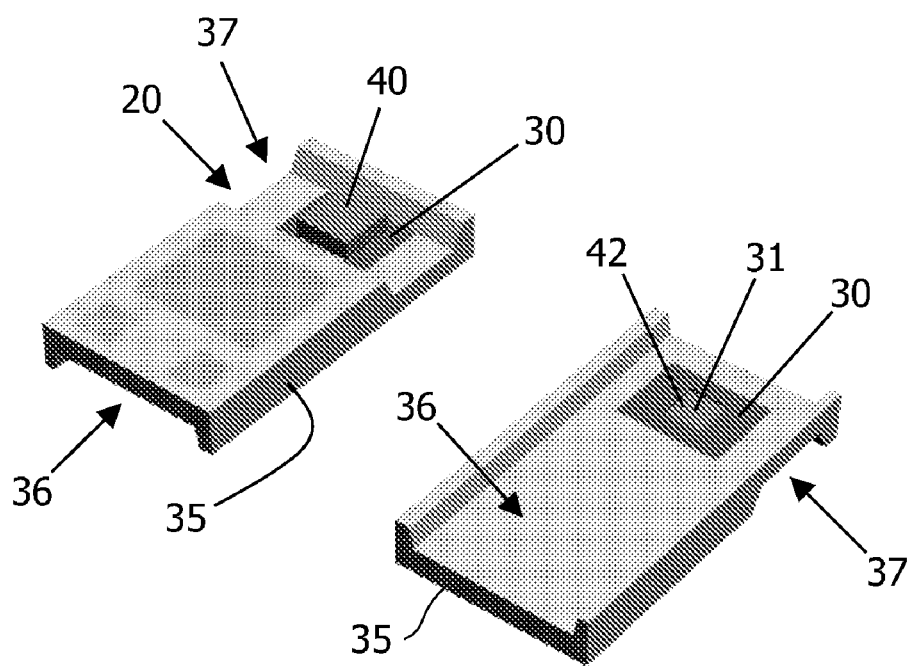

In a fifth step of the process of manufacturing the diagnostic device 2, which is illustrated by FIG. 1e, a sensor die 40 is placed in the recess 37 which is arranged in the under side of the body member 35. Furthermore, the sensor die 40 is connected to the electrically conductive pattern 20 that is present at the under side of the body member 35. In the process, any suitable technique for connecting a die to electrically conductive elements may be applied. The sensor die 40 may be any suitable sensor die, preferably a sensor die made of a semiconductor material.

Figure 1F:
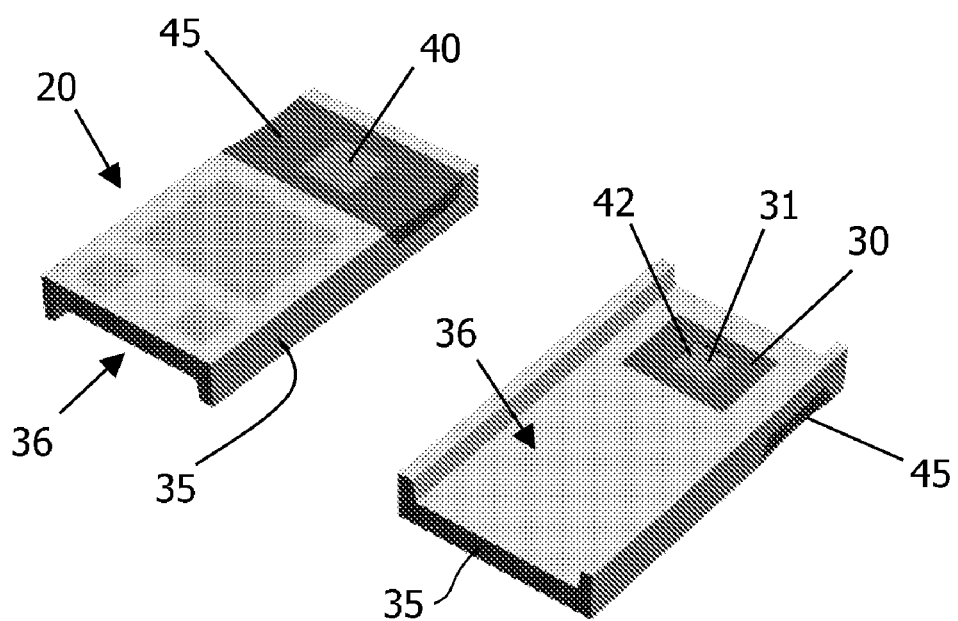

In a sixth step of the process of manufacturing the diagnostic device 2, which is illustrated by FIG. 1f, the recess 37 containing the sensor die 40 is closed by filling the recess 37 with a suitable material such as epoxy resin. In the process, the sensor die 40 gets encapsulated in a filler body 45 which is formed in this way.

Figure 1G:
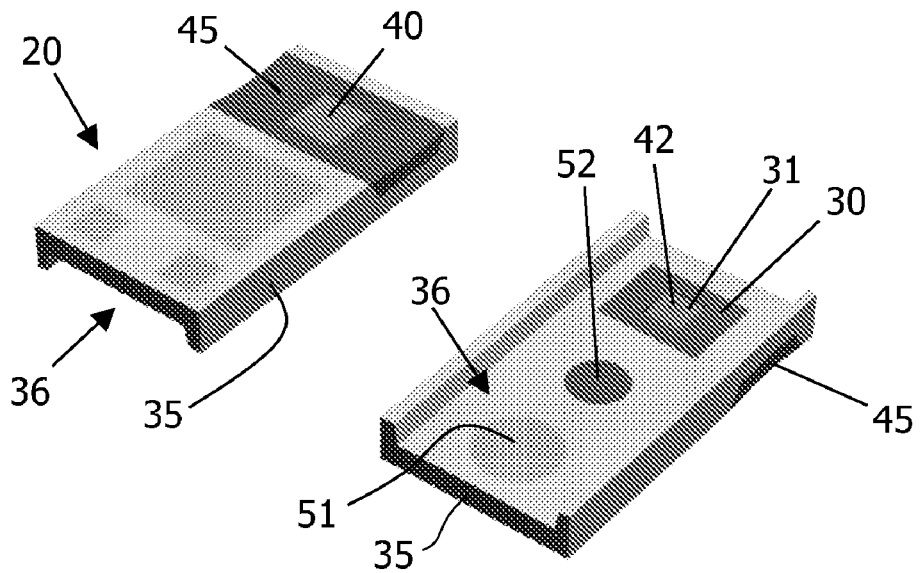

In a seventh step of the process of manufacturing the diagnostic device 2, which is illustrated by FIG. 1g, reagents 51, 52 are applied to the bottom of the open recess 36 that is located at an upper side of the body member 35.

Figure 1H:
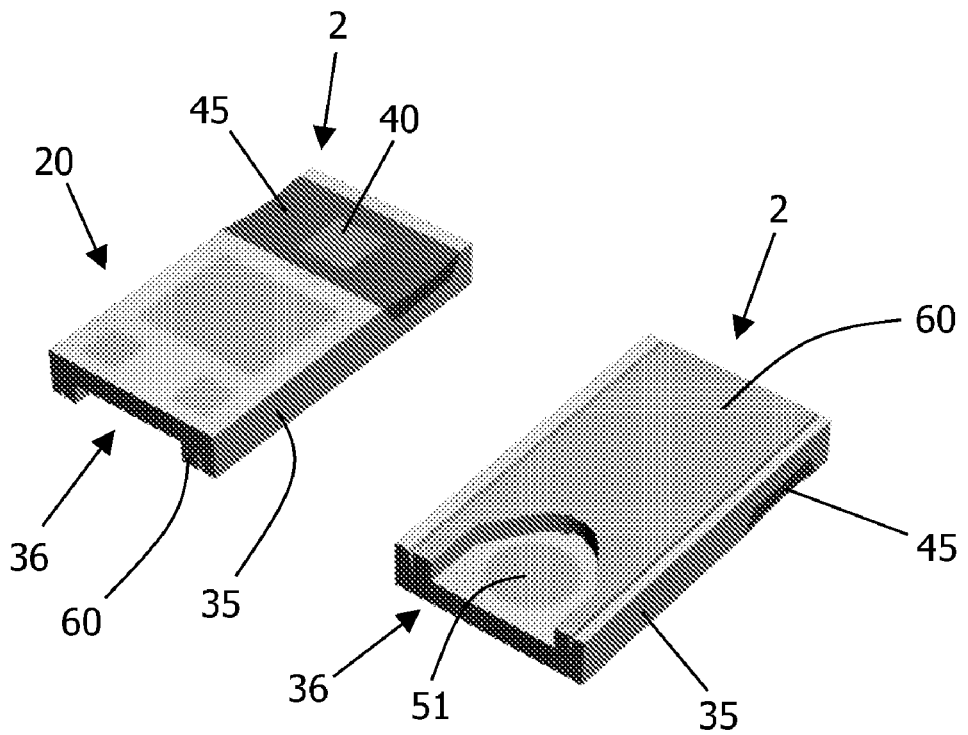
Figure 2:
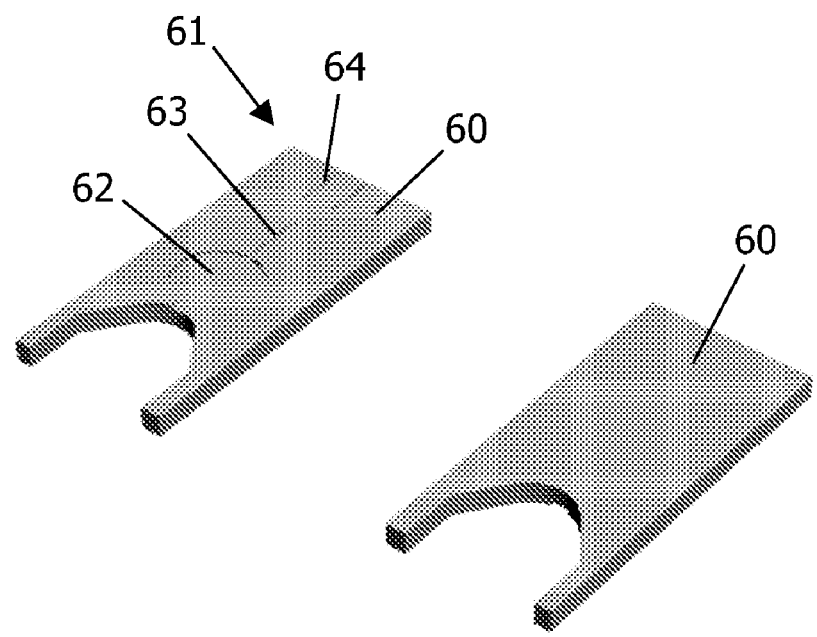
FIG. 2 shows a microfluidic plate which is part of the diagnostic device of the testing device.

In an eighth step of the process of manufacturing the diagnostic device 2, which is illustrated by FIG. 1h, a microfluidic plate 60, which has a pattern 61 of channels for conducting a fluid, which is present at one side of the plate 60, is placed in the recess 36, such that the side of the plate 60 having the pattern 61 of channels faces the bottom of the recess 36. The microfluidic plate 60 is shown in FIG. 2. In the shown example, the microfluidic plate 60 is adapted to leaving one of the reagents 51, 52 uncovered. For the purpose of putting fluid into contact with another of the reagents 51, 52, the microfluidic plate 60 comprises a channel 62 which is shaped like a circular recess. In the following, for sake of clarity, this channel 62 will be referred to as reagent contacting channel 62. For the purpose of supplying the fluid to the sensor die 40, through the hole 31 in the covering member 30, the microfluidic plate 60 comprises a supply channel 63. Furthermore, for the purpose of discharging the fluid from the hole 31, the micro fluidic plate 60 comprises two discharge channels 64.

Within the scope of the present invention, the microfluidic plate 60 may have any suitable shape and comprise any suitable pattern 61 of channels, wherein it is important that the design of the microfluidic plate 60 is adapted to conducting fluid over the reagents 51, 52 and a sensitive surface 42 of the sensor die 40, through the hole 31 in the covering member 30. Furthermore, the microfluidic plate 60 may be manufactured from any suitable material. An example of a suitable material is plastic.

With respect to the sensor die 40, it is noted that this die 40 may for example be a magneto-resistive sensor known per se, which is also generally known as a GMR sensor. In that case, at least one of the reagents 51, 52 comprises magnetic particles or beads which are capable of adhering to certain types of molecules which may be present in the fluid to be tested.

In the diagnostic device 2 which is obtained as a result of the manufacturing process as described on the basis of FIGS. 1a to 1h, the sensor die 40 is safely embedded in the filler body 45, while the sensitive surface 42 of the sensor die 40 is accessible from the upper side of the body member 35, through the hole 31, and the processor die 41 is safely embedded in the body member 35. The recess 37 in which the sensor die 40 is located is obtained in an easy manner, namely by bending a sacrificial carrier 10 in such a way that portions 12, 13 which are located at a different level obtained. At the location of an elevated portion 12 which is formed in the carrier 10 in this way, the recess 37 is automatically obtained when the carrier 10 is covered by material for the purpose of forming the body member 35.

An electric circuit of the diagnostic device 2, which comprises the sensor die 40 and the processor die 41, is connectable to a read-out unit or another electronic device by means of connection pads 21 which lay exposed at the under side of the device 2.

An advantageous feature of the diagnostic device 2 is constituted by the fact that the covering member 30 may be relatively thin, so that the sensitive surface 42 of the sensor die 40 may almost be at the same level as the bottom of the recess 36. As a consequence, it is ensured that the diagnostic device 2 is capable of yielding accurate results during its operation, as the fluid to be examined is passed over the sensitive surface 42 of the sensor die 40 in a controlled manner, wherein the flow of the fluid is practically not disturbed at the location of the hole 31.

Figure 3:
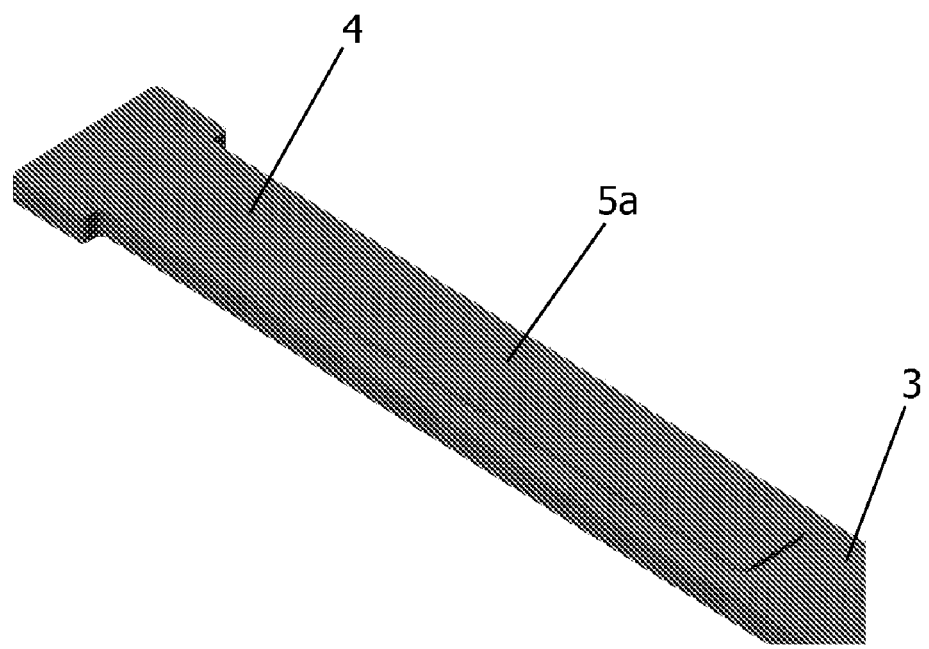
FIG. 3 shows a saliva collecting end of a carrier of the testing device.

The diagnostic device 2 as shown in FIG. 1h is intended to be part of a testing device 1. FIG. 3 shows a portion of this testing device 1. In particular, FIG. 3 shows an end 4 of a carrier 3 of the testing device 1, and a foam member 5a which is arranged on the carrier 3. In the shown example, the carrier 3 is shaped like an elongated piece of strip. Preferably, the carrier 3 comprises a hydrophobic material, whereas the foam of the foam member 5a is a hydrophilic absorbing material. In the following, for sake of clarity, the end 4 of the carrier 3 where the foam member 5a is present will be referred to as saliva collecting end 4.

Figure 4:
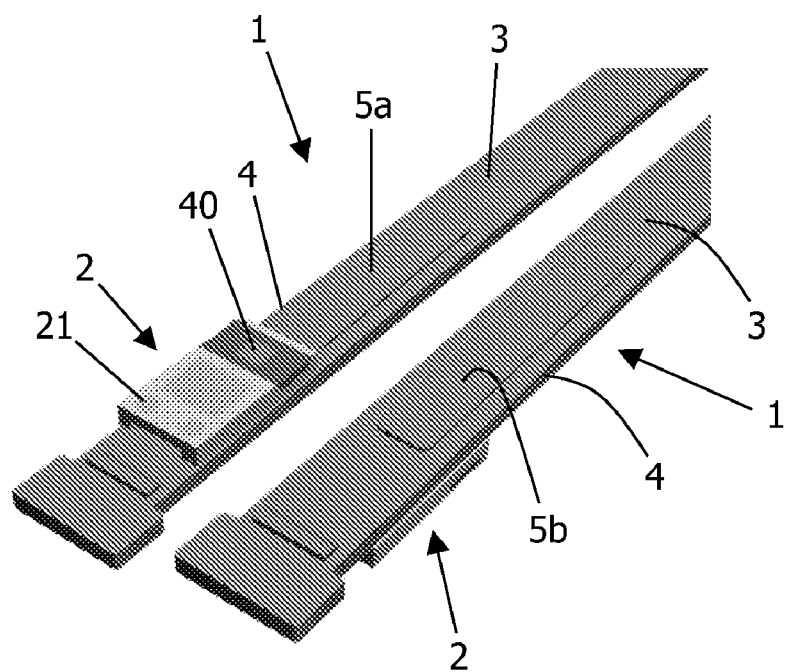
FIG. 4 shows the saliva collecting end of the carrier of the testing device and the diagnostic device.

In FIG. 4, both an upper side and an under side of an assembly of the diagnostic device 2 and the saliva collecting end 4 of the carrier 3 are shown. The diagnostic device 2 is placed on the carrier 3, with the side of the diagnostic device 2 where the microfluidic plate 60 is present down, i.e. facing the carrier 3. FIG. 4 reveals that the testing device 1 comprises two foam members 5a, 5b, which are arranged at different sides of the saliva collecting end 4 of the carrier 3, at corresponding positions.

Figure 5:
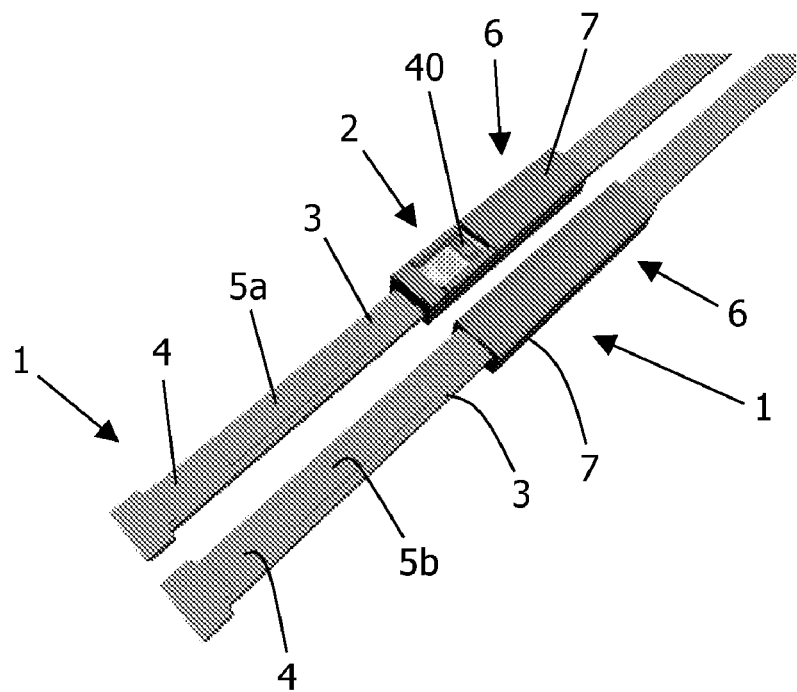
FIG. 5 shows a portion of the carrier of the testing device and a positioning device which is slidably arranged with respect to the carrier, and which encloses the diagnostic device.

In FIG. 5, both an upper side and an under side of a portion of the carrier 3 and a positioning member 6 enclosing the diagnostic device 2 are shown. For sake of clarity, in the Figure, the positioning member 6 is shown with an upper part broken away, so that the diagnostic member 2 is noticeable in the Figure.

The positioning member 6 comprises a sleeve 7 which is slidably arranged around the carrier 3. The diagnostic device 2 is accommodated inside the sleeve 7. By means of the positioning member 6, it is possible to move the diagnostic device 2 with respect to the carrier 3, and to bring the diagnostic device 2 to the saliva collecting end 4 of the carrier 3. An initial position of the positioning member 6 is illustrated by FIG. 5. In this position, the positioning member 6 is located at a distance from the saliva collecting end 4 of the carrier 3. The positioning member 6 is kept in this position when saliva is collected by placing the saliva collecting end 4 of the carrier 3 in the mouth of an individual.

The positioning member 6 is moved from the initial position to a final position after the saliva collecting end 4 of the carrier 3 has been long enough in the mouth of the individual for the foam members 5a, 5b to absorb sufficient amounts of saliva. The positioning member 6 is adapted to holding the diagnostic device 2 in a position in which there is only little space between the microfluidic plate 60 of the diagnostic device 2 and the carrier 3, so that saliva is squeezed from the foam member 5a when the diagnostic device 2 reaches the foam member 5a and is moved across the foam member 5a. In the process, the saliva contacts a first reagent 51, and flows into the reagent contacting channel 62 of the microfluidic plate 60. In this channel 62, the saliva contacts a second reagent 52. Subsequently, the saliva is drawn from the reagent contacting channel 62 under the influence of capillary forces, and flows towards the hole 31 through which the sensitive surface 42 of the sensor die 40 is accessible, through the supply channel 63. The saliva flows out of the hole 31 again, through the discharge channels 64.

The sensor die 40 is adapted to detecting properties of the saliva which is passed over its sensitive surface 42, and which has reacted with the reagents 51, 52. The positioning member 6 is moved with respect to the carrier 3 until the positioning member 6 has reached a final position, which is a position at the saliva collecting end 4 of the carrier 3, in particular a position in which the sleeve 7 encloses both foam members 5a, 5b. The final position of the positioning member 6 is illustrated by FIG. 6.

Figure 6:
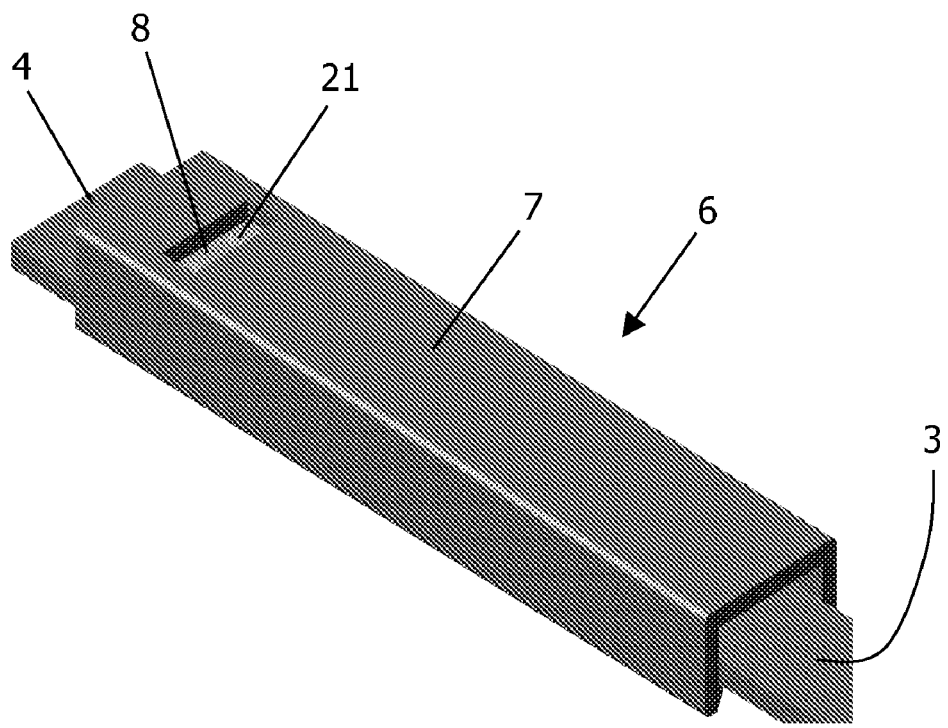
FIG. 6 shows the saliva collecting end of the carrier of the testing device and the positioning device.

It is noted that FIG. 6 shows that the sleeve 7 has a hole 8 for providing access to electrically conductive connection pads 21 of the diagnostic device 2. Consequently, the testing device 1 may easily be connected to a read-out unit for interpreting a signal from the sensor die 40 and displaying the outcome of the interpretation.

When the positioning member 6 is in the final position, the foam member 5b which is present at another side than the side where the diagnostic device 2 is located is safely enclosed by the sleeve 7 of the positioning member 6. In this way, the foam member 5b is prevented from drying out, and the saliva that is present in the foam member 5b may be used in another test, which may be performed with the help of another testing device.

It is very easy for a user to handle the testing device 1 according to the present invention. In the first place, for the purpose of collecting saliva in the foam members 5a, 5b of the testing device 1, the user places the saliva collecting end 4 of the carrier 3 in the mouth of an individual to be tested for a certain period of time. In the second place, the user moves the positioning member 6 from the initial position to the final position. In the third place, the user connects a read-out unit to the diagnostic device 2 that is located inside the positioning member, and checks the output that is generated by this unit.

A particular advantage of the application of the testing device 1 according to the present invention is the fact that the saliva is simply conveyed to the reagents 51, 52 and the sensitive surface 42 of the sensor die 40 when the positioning member 6 is moved from the initial position to the final position, in particular when the diagnostic device 2 is moved across the foam member 5a. There is no need for the user to take any other action than moving the positioning member 6 with respect to the carrier 3.

Figure 7:
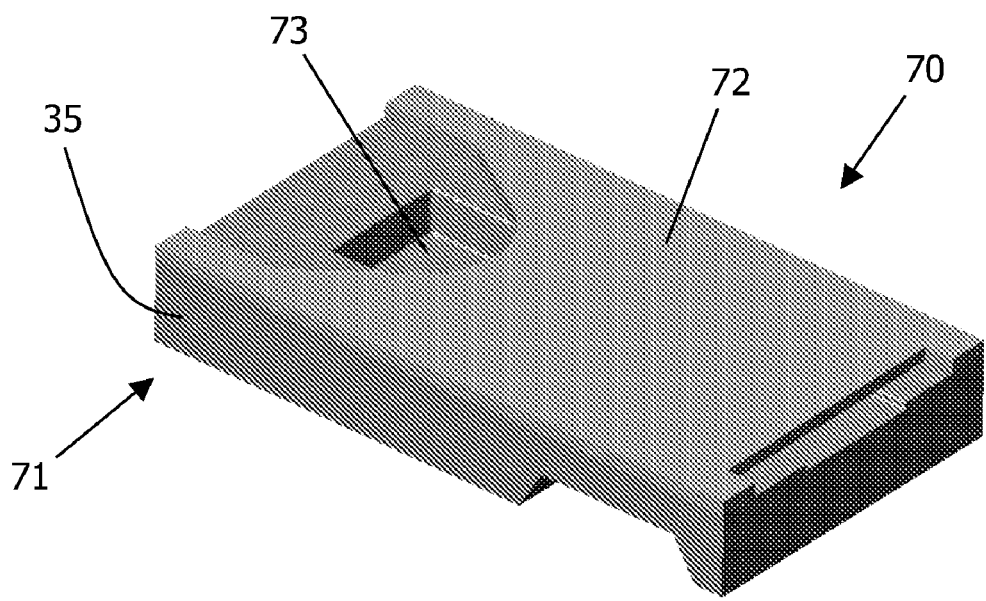
FIG. 7 shows an alternative diagnostic device.
Figure 8:
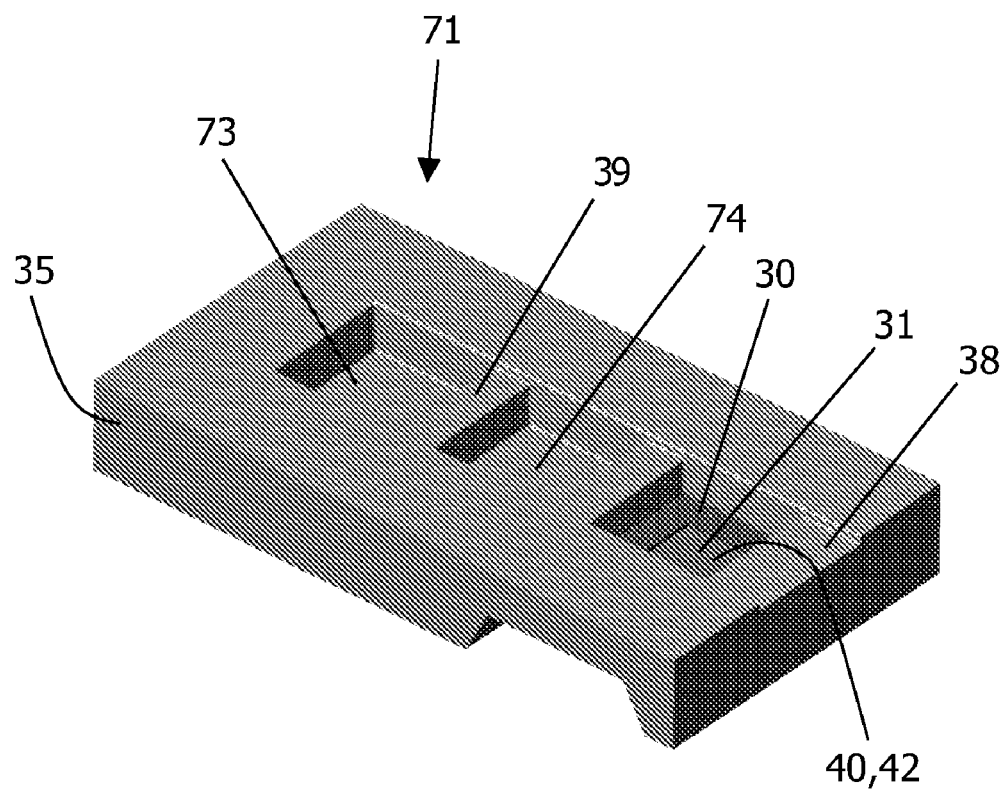
FIG. 8 shows a package of the alternative diagnostic device.

In principle, any suitable diagnostic device may be applied as a part of the testing device 1 according to the present invention. In FIG. 7, an alternative diagnostic device 70 comprising a package 71 and a cover plate 72 which is arranged at one side of the package 71 is shown. The package 71 of the alternative diagnostic device 70 is shown in FIG. 8.

The alternative diagnostic device 70 resembles the diagnostic device 2 which has been described in the foregoing to a large extent. A first notable difference is the fact that the diagnostic device 70 does not comprise a microfluidic plate 60 having a pattern 61 of channels, but comprises a simple cover plate 72 in stead, which does not have any recesses in its surface. A second notable difference is related to the shape of the body member 35. In the alternative diagnostic device 70, the body member 35 comprises more than one recess 36 at the side which is covered by the cover plate 72. In particular, at this side, the body member 35 comprises three recesses 73, 74, 75, which are positioned in a row. A first recess 73, which is referred to as saliva collecting chamber 73, is partially left uncovered by the cover plate 72. A second recess 74, which is referred to as reagents chamber 74, comprises reagents. A bottom of a third recess 75, which is referred to as measuring chamber 75, is constituted by a portion of the covering member 30 having the hole 31 and the sensitive surface 42 of the sensor die 40. A portion 38 of the body member 35 extending between an outer edge of the body member 35 and the measuring chamber 75 is at a lower level with respect to adjacent portions of the body member 35, so that a venting slit for allowing air to escape from the measuring chamber 75 is realized when the cover plate 72 is in place. Portions 39 of the body member 35 which serve as dividing walls between the recesses 73, 74, 75 are at a lower level than adjacent portions of the body member 35 as well, so that slits are also realized between the recesses 73, 74, 75 when the cover plate 72 is in place.

When the positioning member 6 is moved with respect to the carrier 3, and the diagnostic device 70 comes into contact with the foam member 5a, the foam member 5a is impressed, and saliva that is contained by the foam member 5a is squeezed from the foam member 5a into the saliva collecting chamber 73. Subsequently, under the influence of capillary forces, the saliva flows into the reagents chamber 74, where the saliva comes into contact with reagents. In this way, components of the saliva are prepared for detection by the sensor die 40. Finally, the saliva is collected in the measuring chamber 75, where the saliva comes into contact with the sensitive surface 42 of the sensor die 40. In that situation, the sensor die 40 is capable of detecting the presence of at least one specified type of molecules in the saliva and/or determining a quantitative measure such as the concentration of this type of molecules, etc.

In the foregoing, the testing device 1 according to the present invention has been described in the context of performing tests on saliva. On the basis of such tests, it is possible to get an indication if an individual has been using drugs, for example. It is noted that the application of the testing device 1 according to the present invention is not limited to testing saliva. On the contrary, the testing device 1 may be adapted to testing any type of fluid. The fluid may be supplied to the at least one fluid receiving member 5a, 5b of the testing device 1 in any suitable manner.

The testing device 1 according to the present invention offers an advantageous possibility of conveniently putting the diagnostic device into contact with the fluid to be tested. Moreover, the testing device 1 according to the present invention is easy to use, and does not require operation by specialists.

In the foregoing, a device 1 for testing a fluid has been described, which comprises an elongated carrier 3; two foam members 5a, 5b for absorbing the fluid, which are arranged at an end 4 of the carrier 3; a positioning member 6 comprising a sleeve 7 which is slidably arranged on the carrier 3; and a diagnostic device 2, 70, which is arranged in the positioning member 6, and which comprises a sensor die 40 adapted to detecting at least one property of the fluid and means for supplying the fluid to a sensitive surface 42 of the sensor die 40. After the fluid has been supplied to the foam members 5a, 5b, the positioning member 6 is moved towards the end 4 of the carrier 3 where the foam members 5a, 5b are located. When the diagnostic device 2, 70 comes into contact with one of the foam members 5a, 5b, the fluid is squeezed from the foam member 5a and supplied to the sensitive surface 42 of the sensor die 40, through the fluid supplying means of the diagnostic device 2, 70.

Figure 9:
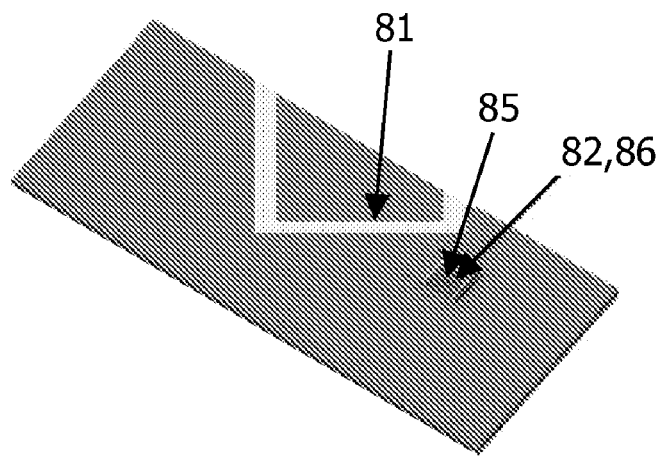
FIG. 9 shows a substrate and a sensor die of an alternative testing device.
Figure 10:
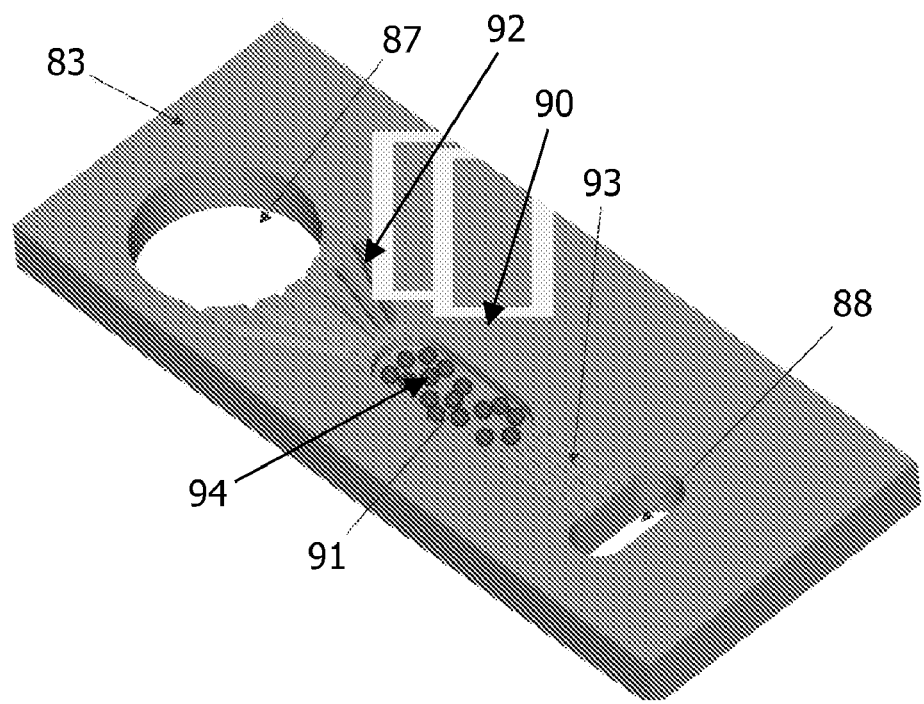
FIG. 10 shows an under side of a microfluidic plate of the alternative testing device.

FIG. 9 shows a substrate 81 and a sensor die 82 of an alternative device 80 for testing a fluid. In particular, the testing device 80 is adapted to receiving an amount of fluid, detecting at least one property of the fluid and to processing output relating to this property. FIG. 10 shows an under side of a microfluidic plate 83 of the testing device 80. FIG. 11 shows an upper side of an assembly of the substrate 81, the sensor die 82 and the microfluidic plate 83 of the testing device 80, wherein also a portion of an electric connection cable 84 is shown. A side view of a longitudinal section of this assembly is diagrammatically shown in FIG. 12. In the following description of the alternative testing device 80, it is assumed that the testing device 80 is adapted to testing saliva, which does not alter the fact that the testing device 80 may just as well be adapted to testing another fluid.

The substrate 81 of the testing device 80 is shaped like a sheet, and is provided with a hole 85. The sensor die 82 is arranged on the substrate 81, at such a position that a sensitive surface 86 of the sensor die 82 is accessible through the hole 85. Preferably, at the side where the sensor die 82 is located, the substrate 81 comprises a pattern (not shown) of electrically conductive pads and electrically conductive tracks. The electric connection cable 84 is connected to this electrically conductive pattern, and serves for connecting the testing device 80 to another electric device, for example a read-out unit.

In the testing device 80, an upper side of the substrate 81 is covered by the microfluidic plate 83. This plate 83 is provided with a saliva receiving hole 87 that is located near one end of the substrate 81, and a venting hole 88 that is located near another end of the substrate 81. At an under side, the microfluidic plate 83 comprises a pattern 90 of recesses. In particular, this pattern 90 comprises a reagents chamber 91, a number of first grooves 92 extending between the saliva receiving hole 87 and the reagents chamber 91, and a number of second grooves 93 extending between the reagents chamber 91 and the venting hole 88. The reagents chamber 91 is filled with dry reagents 94 such as enzymes, magnetic particles or buffer salts. Dimensions of the cross-section of the grooves 92, 93 are in the micrometer range, so that the grooves 92, 93 are capable of filtering the saliva, and of conveying the saliva on the basis of capillary forces.

The way in which the testing device 80 is operated is illustrated on the basis of FIGS. 13a and 13b, in which a side view of a longitudinal section of the assembly of the substrate 81, the sensor die 82 and the microfluidic plate 83 is diagrammatically shown. FIG. 13a shows a droplet of saliva 100 which has just been deposited on the substrate 81, at the position of the saliva receiving hole 87. Subsequently, under the influence of capillary forces, the saliva 100 is drawn towards the reagents chamber 91, through the first grooves 92. In the reagents chamber 91, the reagents 94 are dissolved in the saliva 100. In this way, one or more components of the saliva 100 are put into a detectable state, i.e. a state in which these components are recognizable to the sensor die 82. The saliva mixture 101 thus obtained is conveyed further, through the second grooves 93, until this mixture finally reaches the sensitive surface 86 of the sensor die 82, through the hole 85 in the substrate 81. When the saliva mixture 101 contacts the sensitive surface 86 of the sensor die 82, the sensor die 82 detects one or more pre-determined properties of the saliva 100, and outputs signals representing these properties. The venting hole 88 serves for releasing air from the hole 85 in the substrate 81, so that a situation in which the testing results get influenced by trapped air is avoided. The situation in which the saliva mixture 101 has reached the sensitive surface 86 of the sensor die 82 is illustrated by FIG. 13b.

The sensor die 82 may for example be a magneto-resistive sensor known per se, which is also generally known as a GMR sensor. In that case, the reagents 94 comprise magnetic particles or beads which are capable of adhering to certain types of molecules which may be present in the saliva 100.

An advantage of the application of the fine-meshed network of grooves 92, 93 for conveying the saliva 100 and the saliva mixture 101 is that a situation in which obstructive substances such as dust particles are capable of reaching the hole 85 above the sensor die 82 and influencing the test results does not occur. The testing device 80 does not need much saliva 100 for the purpose of performing its analyzing tasks; it may be sufficient to put only a few microlitres of the saliva 100 inside the saliva receiving hole 87. Moreover, it is very easy for a user to apply the testing device 80 for the purpose of testing a saliva sample. The only thing that the user needs to do is to supply saliva 100 from the sample to the testing device 80, in particular to the saliva receiving hole 87, as the testing device 80 as adapted to performing all steps which are necessary for testing the saliva 100, including the steps of mixing the saliva 100 with reagents 94 and putting the saliva mixture 101 thus obtained into contact with the sensitive surface 86 of the sensor die 82.

Like the testing device 1 as shown in FIG. 5, the testing device 80 as shown in FIG. 11 may comprise a carrier 3, at least one foam member 5a, 5b arranged on the carrier 3, and a positioning member 6 enclosing the substrate 81, the sensor die 82 and the microfluidic plate 83, wherein the positioning member 6 is slidably arranged on the carrier 3 and is capable of bringing the saliva receiving hole 87 in the microfluidic plate 83 at the position of a foam member 5a, such as to receive saliva 100 from the foam member 5a. In the case of such an embodiment of the testing device 1, it is not necessary for a user to use additional means for the purpose of collecting saliva 100, and the only action the user needs to take for the purpose of supplying saliva 100 to an entrance of a testing path leading toward the sensitive surface 86 of the sensor die 82 is displacing the positioning member 6 with respect to the carrier 3.

In a preferred embodiment, the substrate 81 and the microfluidic plate 83 are at least partially transparent, at least at places where the first grooves 92 and/or the second grooves 93 are extending. Furthermore, in this embodiment, the first grooves 92 and/or the second grooves 93 have shapes such as used in Fresnel lenses. In other words, mutual positions and orientations of the first grooves 92 and/or the second grooves 93 are adapted to forming a Fresnel lens, as it were. Consequently, it is possible to check whether the saliva 100 and/or the saliva mixture 101 are actually conveyed toward the sensitive surface 86 of the sensor die 82, even if the saliva 100 is completely transparent, namely by using a light source and measuring the extent to which the light is focused by the first grooves 92 and/or the second grooves 93. When the grooves 92, 93 are empty, the grooves 92, 93 act like a cylindrical lens, and thereby focus light emitted by the light source. When the grooves 92, 93 are filled with fluid, the lens behavior changes due to the fact that the refractive index changes, and the focusing of the light changes. By measuring this change, it is possible to monitor the progress of the saliva 100 and/or the saliva mixture 101 along the testing path. In this way, it is possible to determine an arrival time of the saliva mixture 101 at the sensitive surface 86 of the sensor die 82, which may be used as a factor in a process of controlling the operation of the sensor die 82.

In respect of the preferred embodiment, it is noted that it is important to have a number of first grooves 92 and/or second grooves 93 extending next to each other for the purpose of obtaining the Fresnel lens effect as described. In general, this effect is obtained by having an array of microfluidic channels 92, 93 in the microfluidic plate 83. Preferably, the first grooves 92 extend at least partially parallel with respect to each other, and the same applies to the second grooves 93.

It will be clear to a person skilled in the art that the scope of the present invention is not limited to the examples discussed in the foregoing, but that several amendments and modifications thereof are possible without deviating from the scope of the present invention as defined in the attached claims.

The invention claimed is:

1. A device for testing a fluid, comprising:
   a carrier having two opposite surfaces and distal and proximal ends;
   a fluid receiving member for receiving the fluid, which is arranged on both of the two opposite surfaces of the carrier between the distal and proximal ends;
   a positioning member which is slidably arranged on the carrier; and
   a diagnostic device, which is arranged in the positioning member, and which comprises
      a sensor adapted to detect at least one property of the fluid, and
      one of a cover plate and a microfluidic plate having a first side facing one of the two opposite surfaces of the carrier and adapted to supply the fluid from the fluid receiving member to a surface of the sensor.

2. The device according to claim 1, wherein the plate is adapted to take in the fluid from the fluid receiving member when the first side contacts the fluid receiving member as the positioning member including the diagnostic device and the plate and the fluid receiving member are moved with respect to each other.

3. The device according to claim 1, wherein the plate is adapted to convey the fluid on the basis of capillary forces.

4. The device according to claim 1, wherein the plate comprises a pattern of channels for conducting the fluid, which is present at one side of the plate.

5. The device according to claim 1, wherein the diagnostic device comprises at least one reagent, and wherein the plate is adapted to put the fluid into contact with the at least one reagent.

6. The device according to claim 1, wherein the positioning member forms a sleeve which is slidably arranged around a portion of the carrier between the distal and proximal ends.

7. The device according to claim 1, wherein the positioning member is adapted to enclose the fluid receiving member on both of the two opposite surfaces of the carrier.

8. The device according to claim 1, wherein the diagnostic device comprises at least one electrically conductive connection pad for connection of the diagnostic device to another electric device, and wherein the positioning member comprises at least one hole for providing access to the at least one connection pad.

9. The device according to claim 1, further comprising a display for generating a visual representation of output provided by the sensor during operation of the testing device.

10. The device according to claim 1, wherein the diagnostic device comprises at least one processor die for processing output provided by the sensor during operation of the testing device.

11. The device according to claim 1, wherein the diagnostic device comprises a body member having
   a recess in which the sensor is arranged,
   a pattern of electrically conductive connection pads and electrically conductive tracks arranged on the body member, at the side where the recess is present, the sensor is connected to at least one of the connection pads, and
   at least one hole providing access to the sensor from a side of the body member other than the side where the recess and the electrically conductive pattern are present.

12. The device according to claim 11, wherein the body member of the diagnostic device comprises at least one other recess, arranged perpendicular to the recess in which the sensor is present, and wherein the at least one hole providing access to the sensor is present at a bottom of the at least one other recess.

13. A method of determining a presence and/or a quantity of a compound of a fluid that is supplied to a testing device, the method comprising acts of:
   providing a device including a carrier having two opposite surfaces and distal and proximal ends, a fluid receiving member for receiving the fluid, which is arranged on both of the two opposite surfaces of the carrier between the distal and proximal ends, a positioning member which is slidably arranged on the carrier, and a diagnostic device, which is arranged in the positioning member, and which comprises a sensor adapted to detect at least one property of the fluid, and one of a cover plate and a microfluidic plate having a first side facing one of the two opposite surfaces of the carrier and adapted to supply the fluid from the fluid receiving member to a surface of the sensor;
   supplying the fluid to the fluid receiving member;
   moving the positioning member such that the first side is in contact with the fluid receiving member; and
   the plate conducting the fluid to the sensor surface.

* * * * *